United States Patent
Kouda

(10) Patent No.: US 10,852,939 B2
(45) Date of Patent: Dec. 1, 2020

(54) MEDICAL IMAGE DISPLAY APPARATUS AND RECORDING MEDIUM

(71) Applicant: Konica Minolta, Inc., Tokyo (JP)

(72) Inventor: Youko Kouda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/285,998

(22) Filed: Feb. 26, 2019

(65) Prior Publication Data
US 2019/0302997 A1 Oct. 3, 2019

(30) Foreign Application Priority Data
Mar. 27, 2018 (JP) .................. 2018-059119

(51) Int. Cl.
G06F 3/0488 (2013.01)
G06F 3/0482 (2013.01)
G06F 3/041 (2006.01)
G06F 3/0481 (2013.01)

(52) U.S. Cl.
CPC ........ *G06F 3/04883* (2013.01); *G06F 3/0412* (2013.01); *G06F 3/0416* (2013.01); *G06F 3/0482* (2013.01); *G06F 3/04817* (2013.01)

(58) Field of Classification Search
CPC .............. G06F 3/04883; G06F 3/0416; G06F 3/04817; G06F 3/0412; G06F 3/0482; G16H 40/63; G16H 30/40; G16H 30/20
See application file for complete search history.

(56) References Cited

U.S. PATENT DOCUMENTS

2015/0005630 A1* 1/2015 Jung ............... G06F 19/321
                                                   600/437
2016/0106394 A1* 4/2016 Kang ............... G06F 3/041
                                                   600/437

FOREIGN PATENT DOCUMENTS

JP    2013-132514 A    7/2013
JP    2014-113311 A    6/2014

* cited by examiner

*Primary Examiner* — Andrew Sasinowski
(74) *Attorney, Agent, or Firm* — Lucas & Mercanti, LLP

(57) ABSTRACT

A medical image display apparatus includes a displayer displaying a medical image, a touch panel provided on a display screen of the displayer, a storage storing therein, with respect to the medical image, object position information keeping selectable objects in correspondence with positions thereof, and a hardware processor referring to the object position information, when a long touch operation is performed while the medical image is being displayed; extracting, from among the selectable objects, selectable objects included in a prescribed range from a position in the medical image corresponding to the long touch operation position, as selected candidates; arranging the extracted selected candidates sequentially to be in a selected state in accordance with a touch time period, a touch position, or a touch depth; and confirming, when a finger-off operation is performed, selection of any selected candidate being in the selected state at the time of the finger-off operation.

6 Claims, 10 Drawing Sheets

FIG.2

```
{
"image": {
  "1.2.276.0.7230010.3.1.4.4103543485.4480.1517473028.478": {   /* 31 */
    "1": {
      "measures": [
        {
          "project": "gip",
          "type": "Line",                    // TYPE OF ANNOTATION     /* 32 */
          "measure": {
            "strokeStyle": {
              "shadowOffset": {
                "y": 0,                      // OFFSET VALUE Y USED FOR DRAWING SHADOW
                "x": 0                       // OFFSET VALUE X USED FOR DRAWING SHADOW
              },
              "shadowColor": "#c2c2c2",      // COLOR OF SHADOW
              "shadowBlur": "1"              // BLURRING OF SHADOW
            },
            "visibleShadow": true,           // SHADOW IS DISPLAYED / NOT DISPLAYED
            "color": "#0ff0",                // COLOR OF SHADOW
            "segments": [
              {                                                        /* 33 */
                "y": 91.74061433447099,      // STARTING POINT y
                "x": 31.67235494880546,      // STARTING POINT x
              },
              {                                                        /* 34 */
                "y": 34.075085324232084,     // ENDING POINT y
                "x": 64.87372013651877,      // ENDING POINT x
              }
            ],
            "thickness": "3",                // THICKNESS OF LINE
            "lineType": "SOLID"              // TYPE OF LINE
          }
        },
```

30

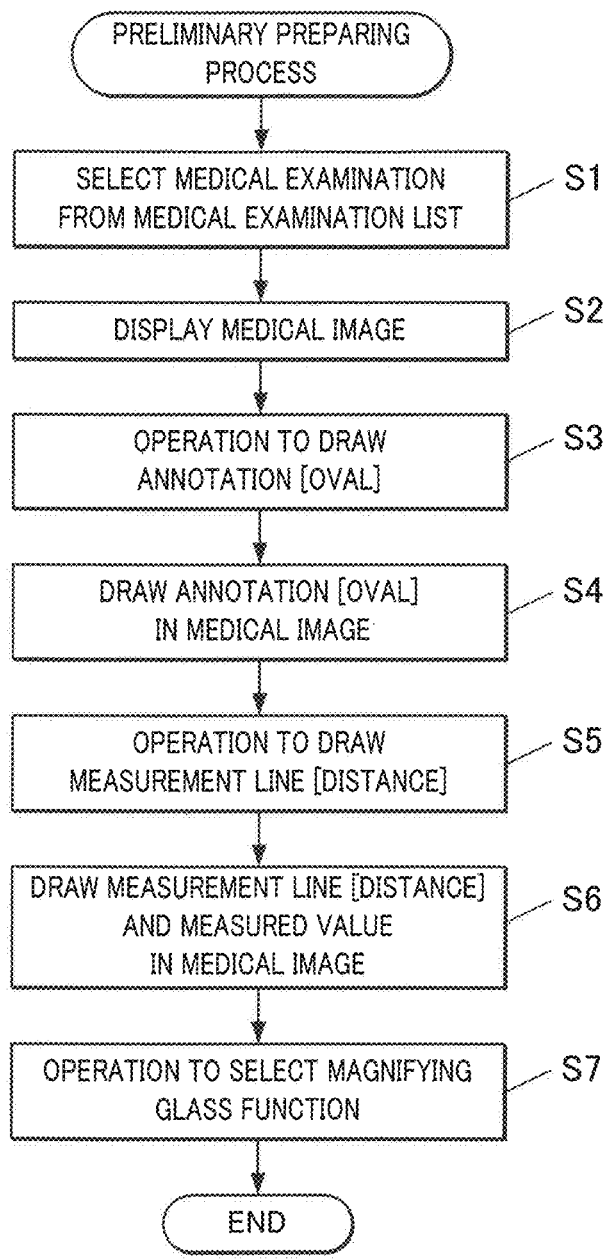

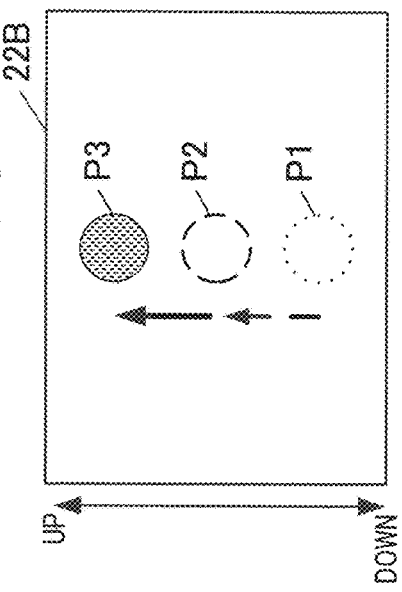
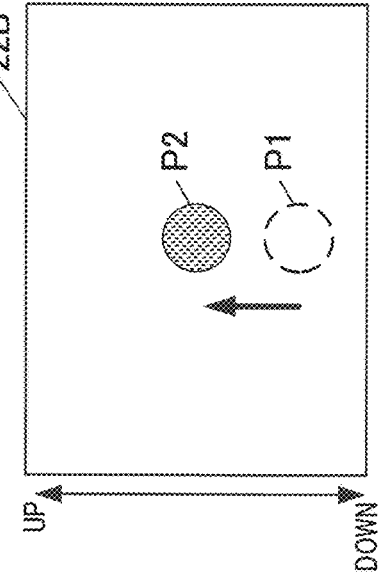
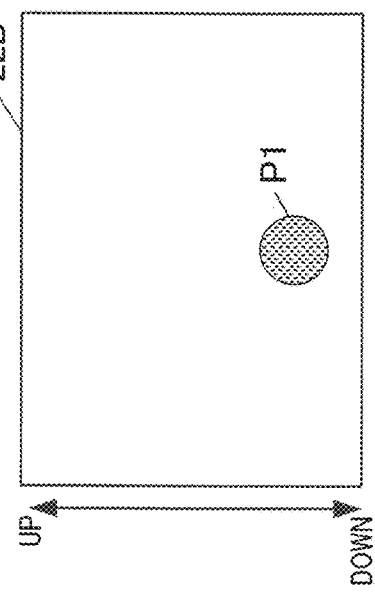
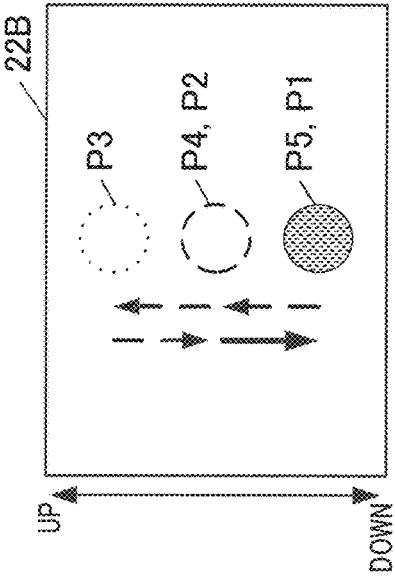
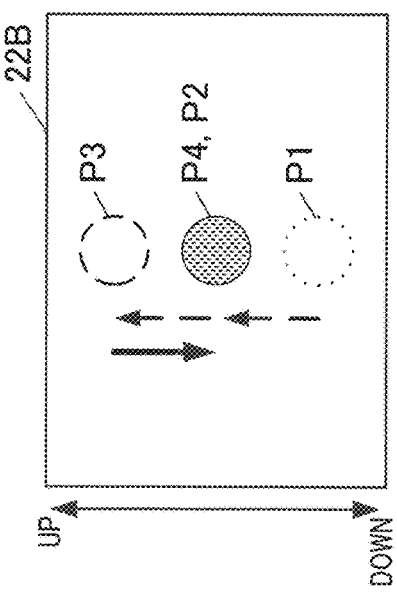

MEDICAL IMAGE DISPLAY APPARATUS AND RECORDING MEDIUM

BACKGROUND

Technological Field

The present invention is related to a medical image display apparatus and a recording medium.

Description of the Related Art

In recent years, digitalization of information has also advanced in the medical field. Medical images taken in various modalities and the like are managed as electronic data. When interpreting a medical image, a medical doctor may draw an annotation such as a straight line, an arrow, a circle, or the like indicating the location of a lesion or may draw a measurement line used for a positional reference for measuring a distance, an angle, or the like, in the medical image displayed on a display device.

To improve the level of precision and efficiency of the interpreting and diagnosing processes performed on a medical image to which a plurality of annotations have been appended, a medical image display apparatus has been proposed (see Japanese Patent Laid-Open No. 2013-132514) by which the plurality of annotations appended to the single medical image are organized into a plurality of groups, so that the annotations belonging to each of the groups are stored while being kept in association with the medical image, in units of the groups. From among the plurality of annotations kept in association with the medical image, the medical image display apparatus is capable of extracting certain annotations belonging to a selected group and displaying the extracted annotations while being superimposed on the medical image.

Further, another medical image display apparatus has also been proposed (see Japanese Patent Laid-Open No. 2014-113311) by which, for each of a plurality of regions into which a medical image is divided, a layer is generated to arrange therein the annotations included in the region, so that the layers are displayed while being superimposed on the medical image. The medical image display apparatus ensures that the display mode of such annotations that are arranged in one of the layers corresponding to the region including a position designated within the medical image is different from the display mode of such annotations that are arranged in the other layers.

However, in the situation where a plurality of annotations and measurement lines are drawn in a medical image, when a user wishes to select one of the drawn elements and to change the position or the size thereof, it may be difficult in some situations to select the desired object when the annotations and the measurement lines are positioned close to one another. In particular, when a touch panel terminal device is being used, it is difficult to designate a position in a fine-tuned manner, compared to situations where a commonly-used PC terminal device operated with a keyboard and a mouse are being used.

Further, in addition to selecting one of the annotations and measurement lines drawn in a medical image, when a user wishes to use, for example, a processing function (e.g., a panning function, a magnifying glass function) to perform a prescribed process on the medical image itself, it is necessary to configure the processing function as a selectable object.

SUMMARY

In view of the issues related to the conventional techniques described above, it is one of the objects of the present invention to improve operability in selecting a selectable object from a medical image.

To achieve at least one of the abovementioned objects, according to a first aspect of the present invention, a medical image display apparatus reflecting one aspect of the present invention includes:

a displayer which displays a medical image;

a touch panel provided on a display screen of the displayer;

a storage which, with respect to the medical image, stores therein object position information which keeps a plurality of selectable objects in correspondence with positions thereof; and a hardware processor which, when a long touch operation is performed on the touch panel while the medical image is being displayed on the displayer, refers to the object position information and extracts, from among the plurality of selectable objects, such selectable objects that are included in a prescribed range from a position in the medical image corresponding to a position of the long touch operation, as selected candidates, further arranges the extracted selected candidates sequentially to be in a selected state in accordance with a touch time period, a touch position, or a touch depth on the touch panel, and when a finger-off operation is performed on the touch panel, confirms selection of any of the selected candidates which is in the selected state at a time of the finger-off operation.

According to a second aspect of the present invention, a non-transitory computer-readable recording medium reflecting one aspect of the present invention stores a program causing a computer of a medical image display apparatus to perform processes, while the medical image display apparatus includes a displayer which displays a medical image, a touch panel provided on a display screen of the displayer, a storage which, with respect to the medical image, stores therein object position information which keeps a plurality of selectable objects in correspondence with positions thereof, the processes including:

referring to the object position information, when a long touch operation is performed on the touch panel while the medical image is being displayed on the displayer; extracting, from among the plurality of selectable objects, such selectable objects that are included in a prescribed range from a position in the medical image corresponding to a position of the long touch operation, as selected candidates; arranging the extracted selected candidates sequentially to be in a selected state in accordance with a touch time period, a touch position, or a touch depth on the touch panel; and confirming, when a finger-off operation is performed on the touch panel, selection of any of the selected candidates which is in the selected state at a time of the finger-off operation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 2 is a drawing illustrating an example of a data structure of annotation data;

FIG. 3 is a flowchart illustrating a preliminary preparing process;

FIG. 8A is a drawing for explaining a method for moving a touch position on a touch panel according to a second embodiment;

FIG. 8B is another drawing for explaining the method for moving the touch position on the touch panel according to the second embodiment;

FIG. 8C is yet another drawing for explaining the method for moving the touch position on the touch panel according to the second embodiment;

FIG. 8D is yet another drawing for explaining the method for moving the touch position on the touch panel according to the second embodiment;

FIG. 8E is yet another drawing for explaining the method for moving the touch position on the touch panel according to the second embodiment;

DETAILED DESCRIPTION OF EMBODIMENTS

Figure 1:
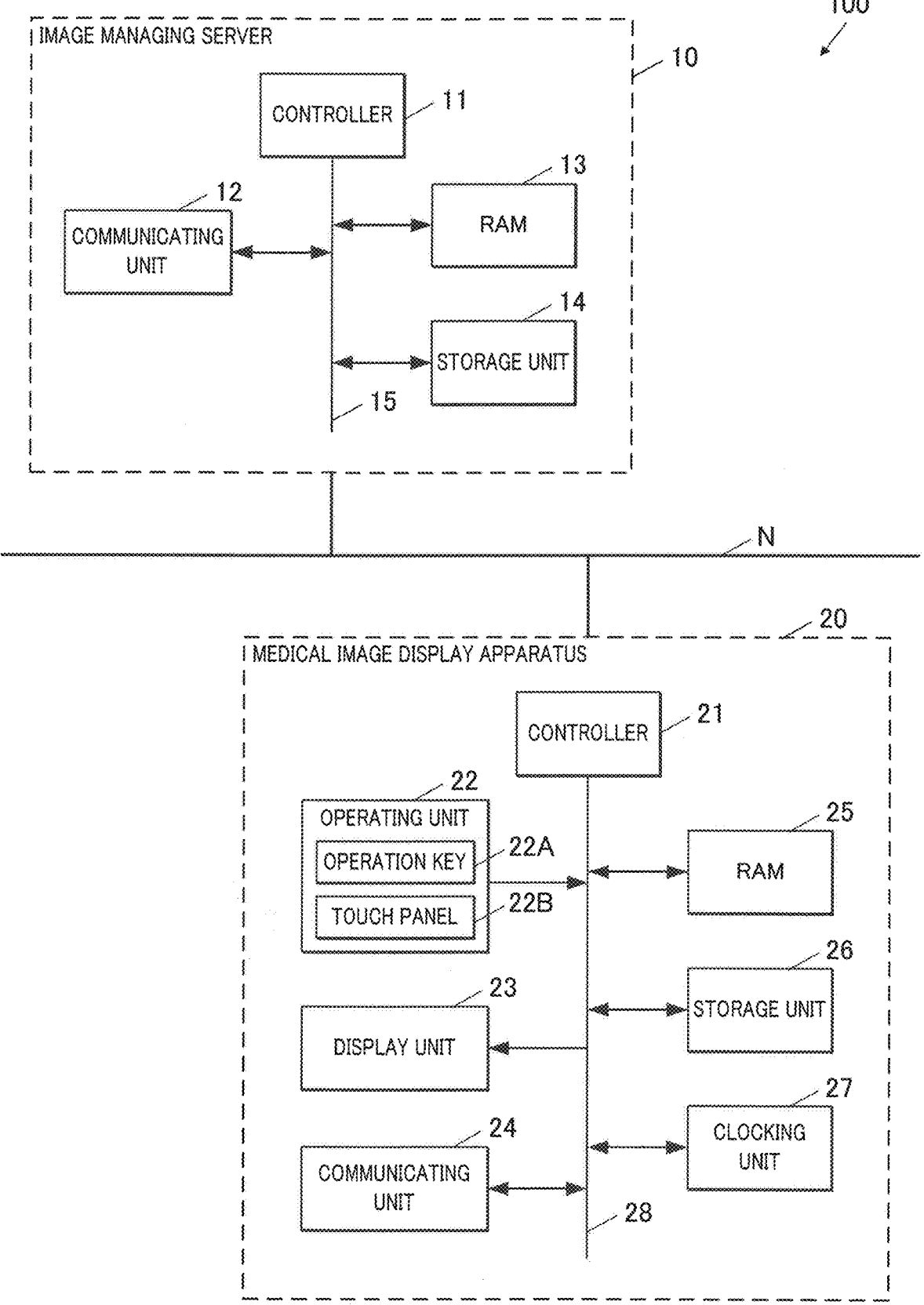
FIG. 1 is a system configuration diagram of a medical image display system according to a first embodiment of the present invention.

Hereinafter, one or more embodiments of the present invention will be described with reference to the drawings. However, the scope of the invention is not limited to the disclosed embodiments.

First Embodiment

To begin with, a first embodiment of the present invention will be explained. The present invention is not limited to the examples illustrated in the drawings.

FIG. 1 illustrates an example of a system configuration of a medical image display system 100.

As illustrated in FIG. 1, the medical image display system 100 includes an image managing server 10 and a medical image display apparatus 20. These apparatuses are connected together so as to be able to transmit and receive data via a communication network N structured with communication lines, such as a Local Area Network (LAN), a Wide Area Network (WAN), or the like. The apparatuses included in the medical image display system 100 are compliant with a Digital Image and Communications in Medicine (DICOM) standard. The communication between the apparatuses is implemented according to the DICOM standard. The quantity of the medical image display apparatuses 20 is not particularly limited.

The image managing server 10 is a computer apparatus that accumulates, stores therein, and manages image data of medical images generated in various modalities (by image taking apparatuses) such as Computed Tomography (CT) apparatuses, Magnetic Resonance Imaging (MRI) apparatuses, Computed Radiography (CR) apparatuses, and the like.

The image managing server 10 is structured so as to include a controller 11, a communicating unit 12, a RAM 13, a storage unit 14, and the like. These functional units are connected together by a bus 15.

The controller 11 is structured by using a Central Processing Unit (CPU) or the like and controls processing operations performed by the functional units of the image managing server 10 in a comprehensive manner. More specifically, the controller 11 reads a system program and various types of processing programs stored in the storage unit 14, loads the read programs into a work area formed in the RAM 13, and performs various types of processes by collaborating with the programs.

The communicating unit 12 is an interface that transmits and receives data to and from external apparatuses such as the medical image display apparatus 20. The communicating unit 12 transmits and receives data to and from apparatuses connected to the communication network N.

The RAM 13 forms the work area that temporarily stores therein the various types of programs read from the storage unit 14, input/output data, parameters, and the like, during the various types of processes of which the execution is controlled by the controller 11.

The storage unit 14 is a storage device structured by using a hard disk, a nonvolatile semiconductor memory, or the like. The storage unit 14 stores therein the system program and the various types of processing programs executed by the controller 11, as well as data required by the execution of these programs.

Further, the storage unit 14 stores therein image data of medical images and an additional information database (DB) storing therein additional information about the medical images in a searchable manner.

Each of the medical images is saved in a DICOM file format compliant with the DICOM standard. A DICOM file is structured with an image part and a header part. The image part has real data of the medical image written thereto, whereas the header part has additional information about the medical image written thereto.

The additional information includes patient information, medical examination information, series information, image information, and the like.

The patient information includes various types of information about the patient such as patient identification information (e.g., a patient ID) used for identifying the patient, as well as the name, the gender, the birthdate, and the like of the patient.

The medical examination information includes various types of information about the medical examination such as medical examination identification information (e.g., a medical examination ID) used for identifying the medical examination, as well as the date and time of the medical examination, the medical doctor in charge, and the like.

The series information includes various types of information about the series such as series identification information (e.g., a series ID) used for identifying the series, as well as the type of the modality used for generating the medical images included in the series, the imaged site, and the like.

The image information includes various types of information about the medical image such as image identification information (e.g., an instance UID) used for identifying the medical image, as well as the date and time at which the image was generated.

In response to a search request from the medical image display apparatus 20, the controller 11 searches in the additional information DB stored in the storage unit 14 for one or more medical examinations (medical images) that match a condition transmitted thereto from the medical image display apparatus 20 and transmits a list of the medical examinations matching the condition, to the medical image display apparatus 20. Further, the controller 11 reads, from the storage unit 14, a medical image requested by the medical image display apparatus 20 to be obtained and transmits the read medical image to the medical image display apparatus 20.

The medical image display apparatus 20 is a tablet terminal device that obtains any of the medical images accumulated and stored in the image managing server 10 and that displays the obtained medical image so as to be interpreted by a medical doctor.

The medical image display apparatus 20 is structured so as to include a controller 21, an operating unit 22, a display unit 23, a communicating unit 24, a RAM 25, a storage unit 26, a clocking unit 27, and the like. These functional units are connected together by a bus 28.

The controller 21 is structured by using a CPU or the like and controls processing operations performed by the functional units of the medical image display apparatus 20 in a comprehensive manner. More specifically, the controller 21 reads a system program and various types of processing programs stored in the storage unit 26, loads the read programs into a work area formed in the RAM 25, and performs various types of processes by collaborating with the programs.

The operating unit 22 includes an operation key 22A such as a power source key used for turning on and off the electric power source; and a touch panel 22B provided on a display screen of the display unit 23. The operating unit 22 outputs an operation signal corresponding to the operation key 22A and an operation signal corresponding to the position of a touch operation performed on the touch panel 22B by a finger of the user or the like, to the controller 21. The operating unit 22 receives various types of operations performed by the user.

The display unit 23 is structured by using a monitor such as a Liquid Crystal Display (LCD) device and displays various types of screens, medical images, and the like according to instructions represented by display signals input thereto from the controller 21.

The communicating unit 24 is an interface that transmits and receives data to and from external apparatuses such as the image managing server 10. The communicating unit 24 transmits and receives data to and from apparatuses connected to the communication network N.

The RAM 25 forms the work area that temporarily stores therein the various types of programs read from the storage unit 26, input/output data, parameters, and the like, during the various types of processes of which the execution is controlled by the controller 21.

The storage unit 26 is a storage device structured by using a hard disk, a nonvolatile semiconductor memory, or the like. The storage unit 26 stores therein the system program and the various types of processing programs executed by the controller 21, as well as data required by the execution of these programs.

Further, as object position information in which a plurality of selectable objects and positions thereof are kept in correspondence with each other with respect to medical images, the storage unit 26 stores therein annotation data, measurement line data, and processing function data.

In the annotation data, the type of an annotation and the position of the annotation are kept in correspondence with each other with respect to the identification information (the instance UID) of the medical image in which the annotation is displayed in a superimposed manner. Examples of the type of the annotation include a straight line (a line segment), an arrow, a circle, a rectangle, a polygon, and the like. The position of the annotation is the position in the medical image in which the annotation is drawn. The position of the annotation may be expressed with the coordinates of the two end points or the coordinates of the center position, when the annotation is a straight line, an arrow, or the like. Alternatively, the position of the annotation may be expressed with information indicating the position of the center of gravity of the annotation or a minimum rectangular region including the annotation.

FIG. 2 illustrates an example of a data structure of annotation data 30. The annotation data 30 includes an instance UID 31 used for identifying the medical image, the type of annotation 32, the annotation positions 33 and 34. In the annotation data 30, "line" is designated as the type of annotation 32; the y coordinate and the x coordinate corresponding to the starting point of the line are recorded as the annotation position 33; and the y coordinate and the x coordinate corresponding to the ending point of the line are recorded as the annotation position 34.

When a plurality of annotations are drawn in a single medical image, it is possible to keep a plurality of types of annotations and the positions thereof in correspondence with the single instance UID.

In the measurement line data, the type of measuring function, the position of the measurement line, a measured value, and the position of the measured value are kept in correspondence with one another with respect to the identification information (the instance UID) of the medical image in which the measurement line is displayed in a superimposed manner. Examples of the type of measuring function include a point-to-point distance measuring function, an angle measuring function, a cardiothoracic ratio measuring function, and the like. The position of the measurement line is the position in the medical image in which the measurement line is drawn. As the position of the measurement line, for example, the coordinates of the starting point and the ending point of the measurement line may be used. The measured value is a value of the distance, the angle, the ratio, or the like that is calculated on the basis of the position of the measurement line, in accordance with the selected measuring function. The position of the measured value is the position in the medical image in which the measured value is drawn.

In the processing function data, a processing function being selected and the position thereof are kept in correspondence with each other with respect to the identification information (the instance UID) of the medical image that is currently displayed. Examples of the processing function include a magnifying glass function, a panning function, an enlarging/reducing function, a gradation function, and the like. The position kept in correspondence with any of these processing functions is the region of the entire medical image.

The clocking unit 27 measures an elapsed time period since each of the selected candidates extracted from among a plurality of selectable objects is brought into a selected state, during a first object selecting process (see FIG. 4), and further outputs the elapsed time periods to the controller 21.

The controller 21 obtains any of the medical images stored in the storage unit 14 of the image managing server 10 and causes the display unit 23 to display the obtained medical image.

The controller 21 arranges one or more annotations and/or measurement lines to be displayed in the medical image displayed on the display unit 23.

When a long touch operation (a long press: a state in which the touch panel 22B recognizes as being touched) is performed on the touch panel 22B while a medical image is being displayed on the display unit 23, the controller 21 refers to the object position information (the annotation data, the measurement line data, and the processing function data) and extracts, from among the plurality of selectable objects, such selectable objects that are included in a prescribed range from the position in the medical image corresponding to the position of the long touch operation, as selected candidates. Whether a long touch operation was performed or not is determined on the basis of whether or not a touch operation performed on the touch panel 22B has lasted for a period of time equal to or longer than a prescribed length. The long touch operation continues as long as the touch panel 22B is recognizing as being touched and ends when the touch is cancelled (at the time of a finger-off operation). Further, as the prescribed range, for example, a region that is within a prescribed distance from and is centered on the position in the medical image corresponding to the position of the long touch operation may be used. Further, it is possible to arbitrarily change the prescribed range. When any of the selectable objects is not structured as a single point but spreads two-dimensionally, it is acceptable to regard the selectable object as a selected candidate when at least a part of the selectable object is included in the prescribed range.

Each of the selectable objects may be an annotation drawn in a medical image, a measurement line drawn in a medical image, or a processing function used for performing a prescribed process on a medical image.

In the processing function data, the position kept in correspondence with each processing function is the entirety of the medical image. Accordingly, no matter to which position in the medical image the position of the long touch operation corresponds, the processing function is extracted as one of the selected candidates so long as the processing function is selected.

In accordance with the touch time period of the long touch operation performed on the touch panel 22B, the controller 21 sequentially arranges the extracted selected candidates to be in a selected state.

When the finger-off operation (to take the finger off the screen) is performed on the touch panel 22B, the controller 21 confirms selection of the selected candidate that is in the selected state at the time of the finger-off operation.

When the selected candidate of which the selection has been confirmed is either an annotation or a measurement line, the controller 21 corrects either the position or the size of the selected candidate, which is the annotation or the measurement line, on the basis of an operation performed on the touch panel 22B.

The confirmation of selection of the processing function is to allocate a prescribed operation performed on the touch panel 22B to an event that executes the processing function.

For example, when selection of the magnifying glass function has been confirmed, a touch operation performed on the touch panel 22B is allocated to an event that executes an image processing process to enlarge, by a predetermined enlargement ratio, a prescribed region centered on the position in the medical image corresponding to the touch position.

When selection of the panning function has been confirmed, a drag operation (a slide operation) performed on the touch panel 22B is allocated to an event that changes a displayed range within the medical image.

When the enlarging/reducing function has been confirmed, a drag operation performed on the touch panel 22B is allocated to an event that enlarges or reduces the medical image. More specifically, the image can be enlarged by an upward drag operation, whereas the image can be reduced by a downward drag operation.

When the gradation function has been confirmed, a drag operation performed on the touch panel 22B is allocated to an event that changes a Window Center (WC) value or a Window Width (WW) value in a gradation process performed on the medical image. More specifically, the WC value can be changed by drag operations in left-and-right directions, whereas the WW value can be changed by drag operations in up-and-down directions.

Next, operations performed in the first embodiment will be explained.

FIG. 3 is a flowchart illustrating a preliminary preparing process performed by the medical image display apparatus 20. This process is realized by a software process implemented by collaboration between the controller 21 and a program stored in the storage unit 26. In the following sections, an example using an oval annotation, a distance measurement line, and the magnifying glass function will be explained.

At first, the controller 21 obtains a medical examination list from the image managing server 10 and causes the display unit 23 to display the obtained medical examination list. When the user selects a medical examination from the medical examination list by performing an operation on the touch panel 22B (step S1), the controller 21 obtains a medical image taken during the selected medical examination from the image managing server 10 and causes the display unit 23 to display the obtained medical image (step S2).

Subsequently, when an operation to draw an oval annotation is received through an operation performed on the touch panel 22B by the user (step S3), the controller 21 draws the oval annotation in the medical image displayed on the display unit 23 (step S4). More specifically, on the touch panel 22B, the user selects an icon corresponding to a drawing function to draw the oval annotation and designates a position in which the oval is to be drawn in the medical image. The controller 21 stores annotation data into the storage unit 26, the annotation data keeping the instance UID of the medical image being displayed, the type of annotation (the oval), the position of the annotation, and the like in correspondence with one another.

After that, when an operation to draw a measurement line used for measuring a distance is received through an operation performed on the touch panel 22B by the user (step S5), the controller 21 draws the distance measurement line and a measured value in the medical image displayed on the display unit 23 (step S6). More specifically, when the user selects an icon corresponding to the distance measuring function on the touch panel 22B and designates a starting point and an ending point of the measurement line in the medical image, the controller 21 calculates the distance between the two points (the measured value). The controller 21 stores measurement line data into the storage unit 26, the measurement line data keeping the instance UID of the medical image being displayed, the type of measuring function (distance); the position of the measurement line, the measured value, the position of the measured value, and the like in correspondence with one another.

After that, the controller 21 receives an operation to select the magnifying glass function through an operation performed on the touch panel 22B by the user (step S7). More specifically, the user selects an icon corresponding to the magnifying glass function on the touch panel 22B. The controller 21 stores processing function data into the storage unit 26, the processing function data keeping the instance UID of the medical image being displayed, the processing function (the magnifying glass function) corresponding to the selected icon, the position indicating the entire medical image, and the like are kept in correspondence with one another.

The preliminary preparing process has thus been finished.

Figure 4:
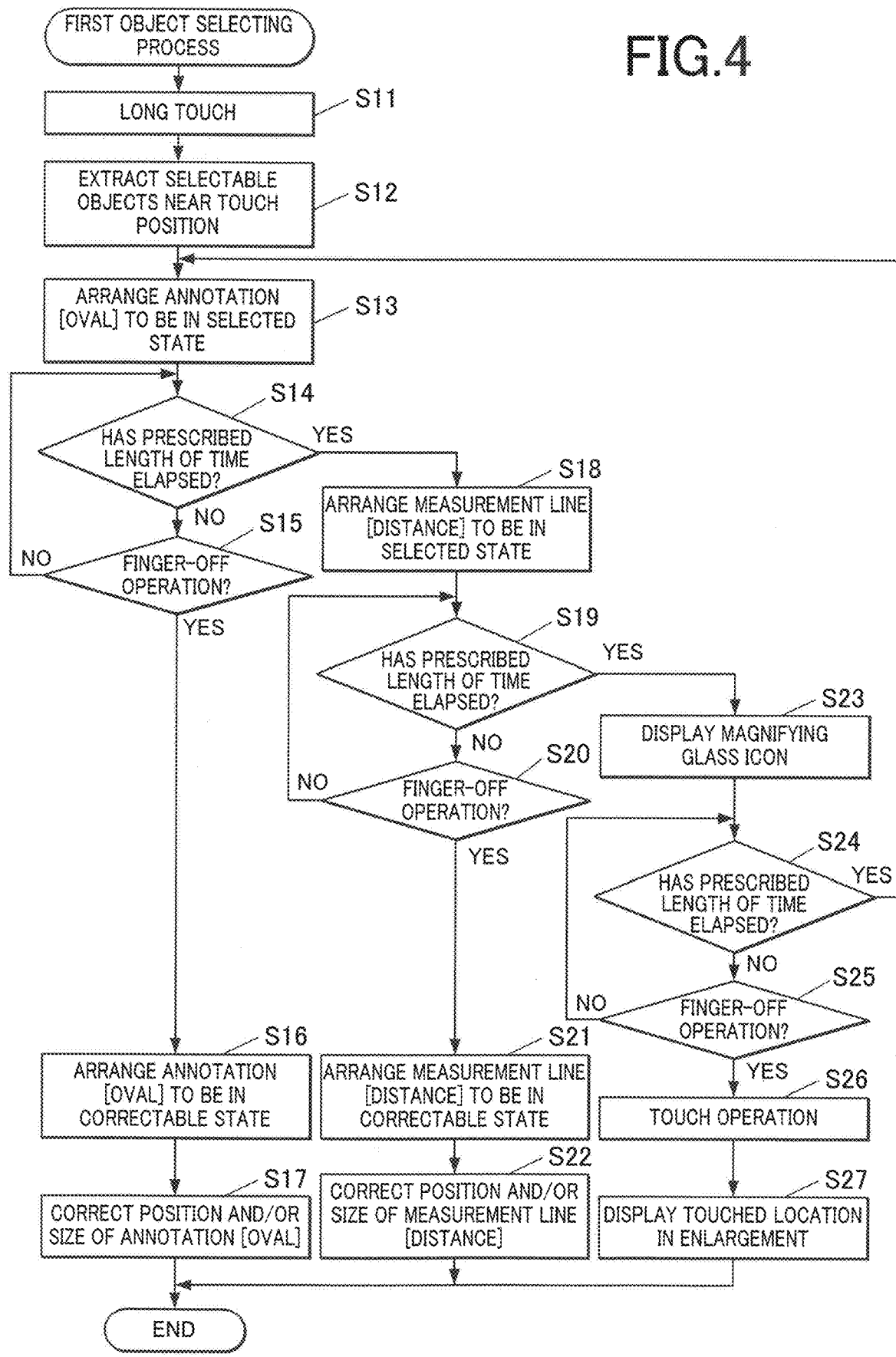
FIG. 4 is a flowchart illustrating a first object selecting process.

FIG. 4 is a flowchart illustrating the first object selecting process performed by the medical image display apparatus 20. This process is performed subsequent to the preliminary preparing process and is realized by a software process implemented by collaboration between the controller 21 and a program stored in the storage unit 26.

When a long touch operation is performed on the touch panel 22B by the user (step S11), the controller 21 extracts selectable objects positioned near the touch position (step S12). More specifically, the controller 21 refers to the object position information (the annotation data, the measurement line data, and the processing function data) and extracts, from among the annotation drawn in the medical image, the measurement line drawn in the medical image, and the processing function selected for the medical image, such selectable objects (the oval annotation, the distance measurement line, and the magnifying glass function) of which the positions are included in a prescribed range from the position in the medical image corresponding to the position of the long touch operation, as selected candidates.

In the following sections, an example will be explained in which all of the three selectable objects are extracted as the selected candidates. However, the extracted selected candidates may vary depending on the positions of the selectable objects and the setting of the prescribed range.

Further, prescribed order ranking is allocated to the extracted selected candidates. In the present example, the order ranking is determined as: the oval annotation, the distance measurement line, and the magnifying glass function.

Subsequently, the controller 21 arranges the oval annotation displayed on the display unit 23 to be in a selected state (step S13).

Figure 5A:
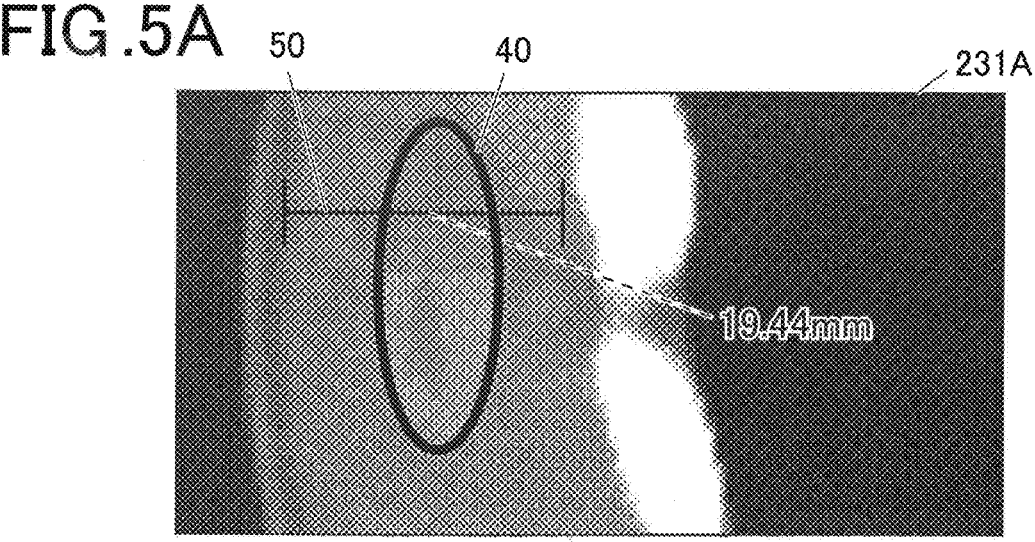
FIG. 5A is an example of a viewer screen in which an oval annotation is in a selected state.

FIG. 5A illustrates an example of a viewer screen 231A displayed on the display unit 23. The viewer screen 231A displays a medical image serving as a display target, while an oval annotation 40 and a distance measurement line 50 are displayed in the medical image while being superimposed thereon. In the present example, the bold line used for drawing the oval annotation 40 indicates that the oval annotation 40 is in the selected state. Alternatively, it is also acceptable to indicate that the oval annotation 40 is in a selected state by arranging the display mode (e.g., the color, the type of the line, or the like) of the oval annotation to be different from display modes of the other selected candidates.

Subsequently, the controller 21 causes the clocking unit 27 to measure the elapsed time period since the oval annotation is brought into the selected state. The controller 21 judges whether or not the time period measured by the clocking unit 27 exceeds a prescribed length of time (step S14).

When the prescribed length of time has not elapsed since the oval annotation was brought into the selected state (step S14: No), the controller 21 judges whether or not a finger-off operation has been performed on the touch panel 22B by the user (step S15).

When the finger-off operation has not been performed (step S15: No), the process returns to step S14, so that the processing is repeatedly performed.

On the contrary, when it is determined at step S15 that the finger-off operation has been performed (step S15: Yes), the controller 21 confirms the selection of the oval annotation that was in the selected state at the time of the finger-off operation and further arranges the oval annotation to be in a correctable state (step S16).

Figure 5B:
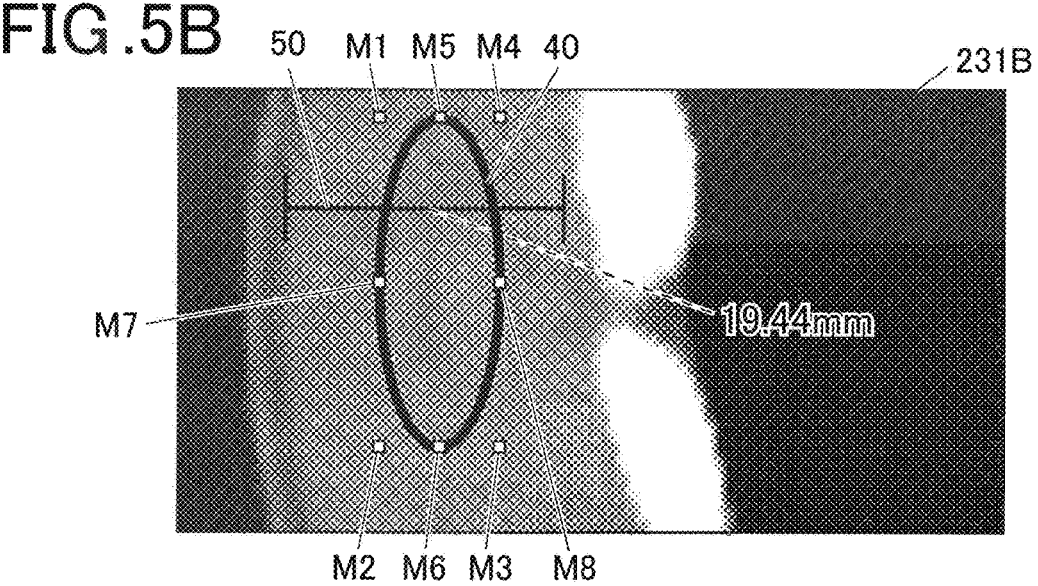
FIG. 5B is another example of a viewer screen in which selection of the oval annotation has been confirmed.

For example, as illustrated in FIG. 5B, on a viewer screen 231B, editing marks M1 to M8 are displayed in the medical image at the four corners of the rectangular region enclosing the oval annotation 40 as well as the two end points of the major axis and the two end points of the minor axis of the oval, so as to indicate that the oval annotation 40 is in the correctable state.

Subsequently, according to an operation performed on the touch panel 22B by the user, the controller 21 corrects the position and/or the size of the oval annotation (step S17). For example, the controller 21 moves the position of the entire oval, changes the size of the oval in the major axis direction and the minor axis direction, and/or rotates the oval. In accordance with the corrections made on the position and/or the size of the oval annotation, the controller 21 updates the annotation data stored in the storage unit 26.

Figure 5C:
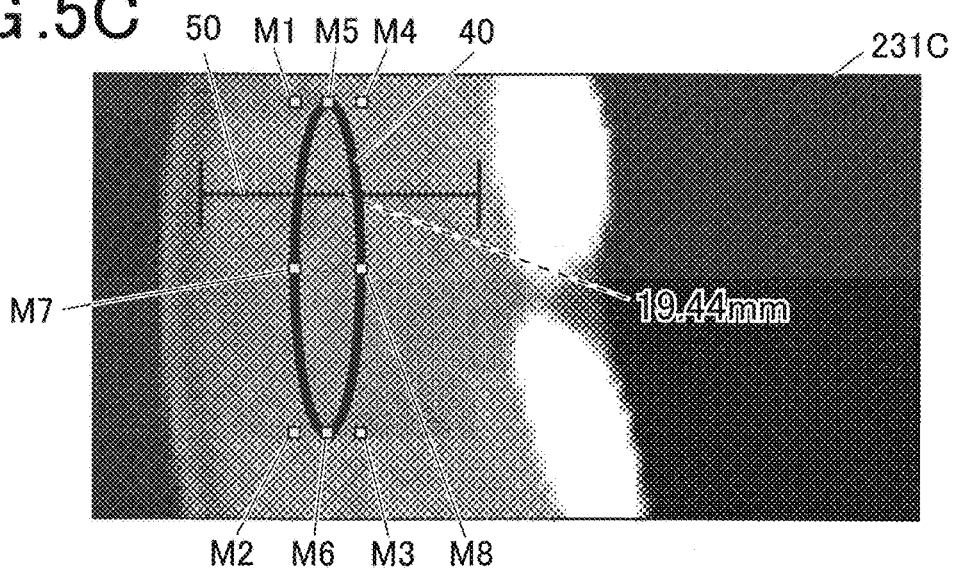
FIG. 5C is yet another example of a viewer screen in which the oval annotation has been corrected.

FIG. 5C illustrates an example of a viewer screen 231C observed after the oval annotation is corrected. On the viewer screen 231C, the size (the distance between M7 and M8) of the oval annotation 40 in the minor axis direction is smaller than that in FIG. 5B.

When it is determined at step S14 that the prescribed length of time has elapsed since the oval annotation was brought into the selected state (step S14: Yes), the controller 21 arranges the distance measurement line displayed on the display unit 23 to be in a selected state (step S18).

Figure 6A:
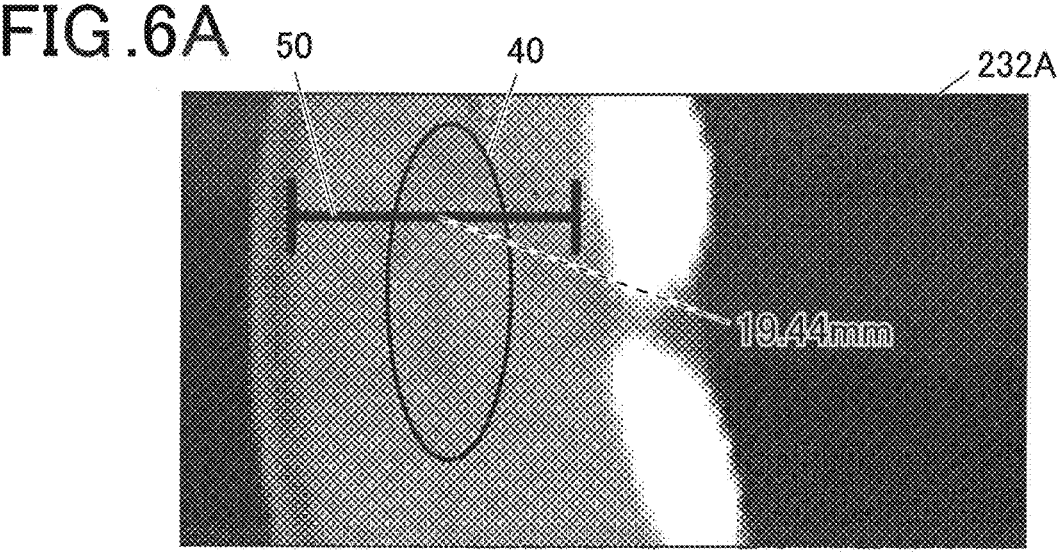
FIG. 6A is an example of a viewer screen in which a distance measurement line is in a selected state.

As illustrated in FIG. 6A, on a viewer screen 232A displayed on the display unit 23, of the oval annotation 40 and the distance measurement line 50 that are displayed in the medical image in a superimposed manner, the distance measurement line 50 is in a selected state. In the present example, the bold line used for drawing the distance measurement line 50 indicates that the distance measurement line 50 is in the selected state. Alternatively, it is also acceptable to indicate that the measurement line 50 is in a selected state by arranging the display mode (e.g., the color, the type of the line, or the like) of the measurement line to be different from display modes of the other selected candidates.

Subsequently, the controller 21 causes the clocking unit 27 to measure the elapsed time period since the distance measurement line is brought into the selected state. The controller 21 judges whether or not the time period measured by the clocking unit 27 exceeds a prescribed length of time (step S19).

When the prescribed length of time has not elapsed since the distance measurement line was brought into the selected state (step S19: No), the controller 21 judges whether or not a finger-off operation has been performed on the touch panel 22B by the user (step S20).

When the finger-off operation has not been performed (step S20: No), the process returns to step S19, so that the processing is repeatedly performed.

On the contrary, when it is determined at step S20 that the finger-off operation has been performed (step S20: Yes), the controller 21 confirms the selection of the distance measurement line that was in the selected state at the time of the finger-off operation and further arranges the distance measurement line to be in a correctable state (step S21).

Figure 6B:
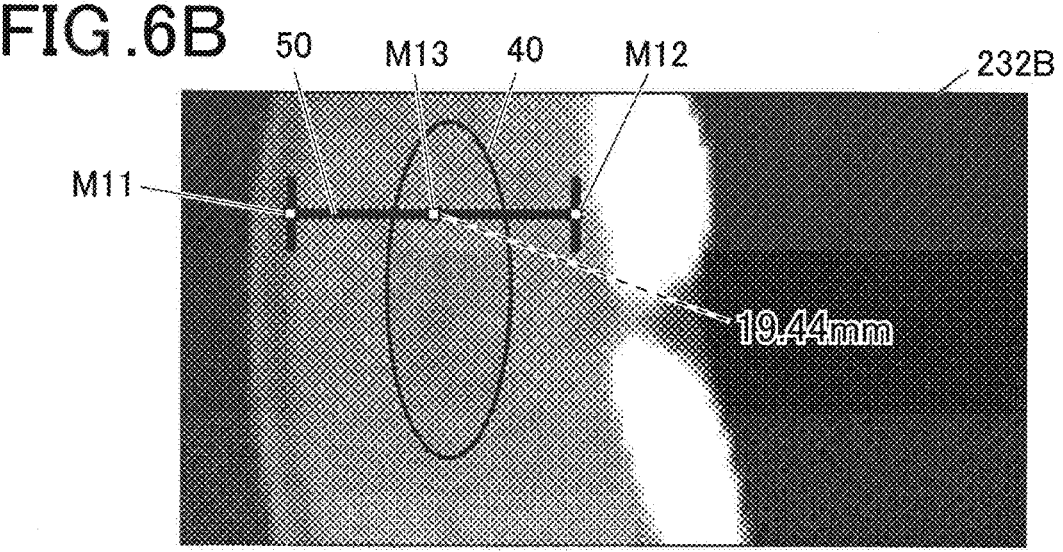
FIG. 6B is another example of a viewer screen in which selection of the distance measurement line has been confirmed.

For example, as illustrated in FIG. 6B, on a viewer screen 232B, editing marks M11 to M13 are displayed at the two end points and the center position of the distance measurement line 50 in the medical image, so as to indicate that the distance measurement line 50 is in the correctable state.

Subsequently, the controller 21 corrects the position and/or the size of the distance measurement line according to an operation performed on the touch panel 22B by the user (step S22). For example, the controller 21 may move the position of the entire measurement line or may change the positions of the starting point and/or the ending point of the measurement line. In accordance with the corrections made on the position and/or the size of the distance measurement line, the controller 21 updates the measurement line data stored in the storage unit 26.

Figure 6C:
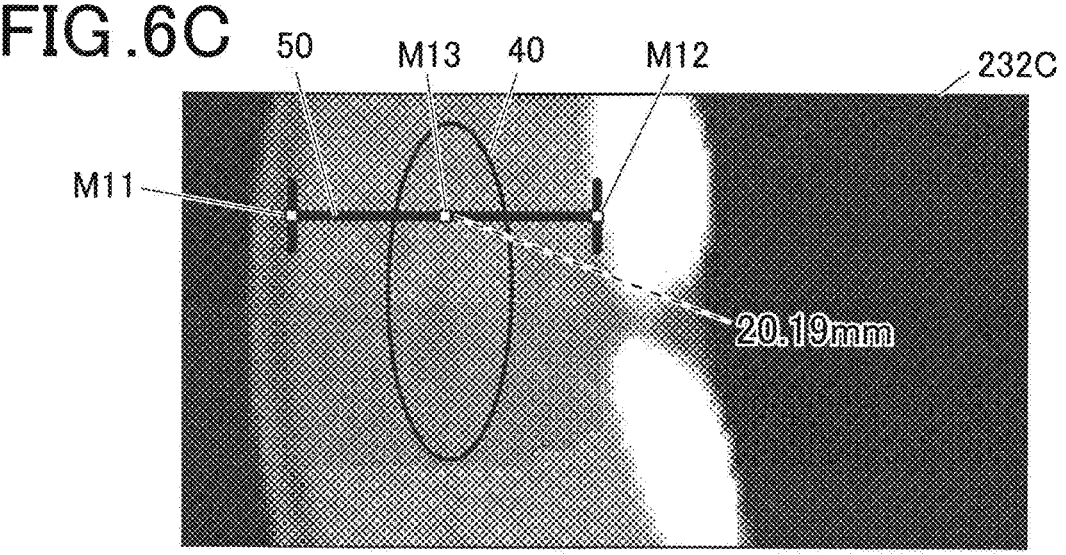
FIG. 6C is yet another example of a viewer screen in which the distance measurement line has been corrected.

FIG. 6C illustrates an example of a viewer screen 232C observed after correcting the distance measurement line. On the viewer screen 232C, the distance measurement line 50 is longer on the right side compared to that in FIG. 6B. In accordance with the correction of the distance measurement line 50, the measured value has also been changed from "19.44 mm" to "20.19 mm".

When it is determined at step S19 that the prescribed length of time has elapsed since the distance measurement line was brought into the selected state (step S19: Yes), the controller 21 arranges the magnifying glass function to be in a selected state and causes the display unit 23 to display a magnifying glass icon (step S23).

Figure 7A:
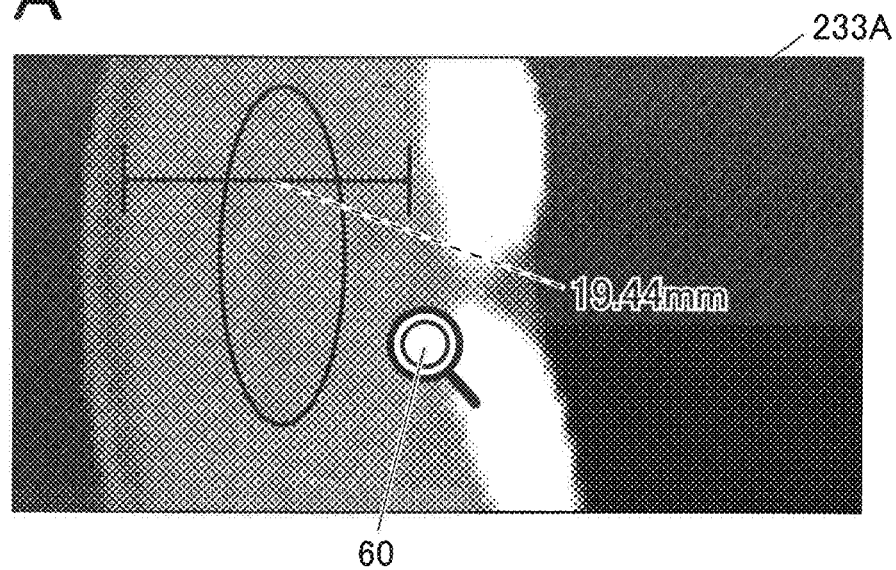
FIG. 7A is an example of a viewer screen in which a magnifying glass function is in a selected state.

As illustrated in FIG. 7A, on a viewer screen 233A displayed on the display unit 23, a magnifying glass icon 60 is displayed. In the present example, by the magnifying glass icon 60 being displayed, it is indicated that the magnifying glass function is in the selected state.

Subsequently, the controller 21 causes the clocking unit 27 to measure the elapsed time period since the magnifying glass icon is displayed. The controller 21 judges whether or not the time period measured by the clocking unit 27 exceeds a prescribed length of time (step S24).

When the prescribed length of time has elapsed since the magnifying glass icon was displayed (step S24: Yes), the process returns to step S13 (see FIG. 5A).

On the contrary, when it is determined at step S24 that the prescribed length of time has not elapsed since the magnifying glass icon was displayed (step S24: No), the controller 21 judges whether or not a finger-off operation has been performed on the touch panel 22B by the user (step S25).

When the finger-off operation has not been performed (step S25: No), the process returns to step S24, so that the processing is repeatedly performed.

On the contrary, when it is determined at step S25 that the finger-off operation has been performed (step S25: Yes), the controller 21 confirms the selection of the magnifying glass function that was in the selected state at the time of the finger-off operation and further arranges the magnifying glass function to be in an executable state. More specifically, the controller 21 allocates a prescribed operation (the touch operation) performed on the touch panel 22B to an event that executes the magnifying glass function.

When a touch operation is performed on the touch panel 22B by the user (step S26), the controller 21 displays, in enlargement, the touched location of the medical image (step S27).

Figure 7B:
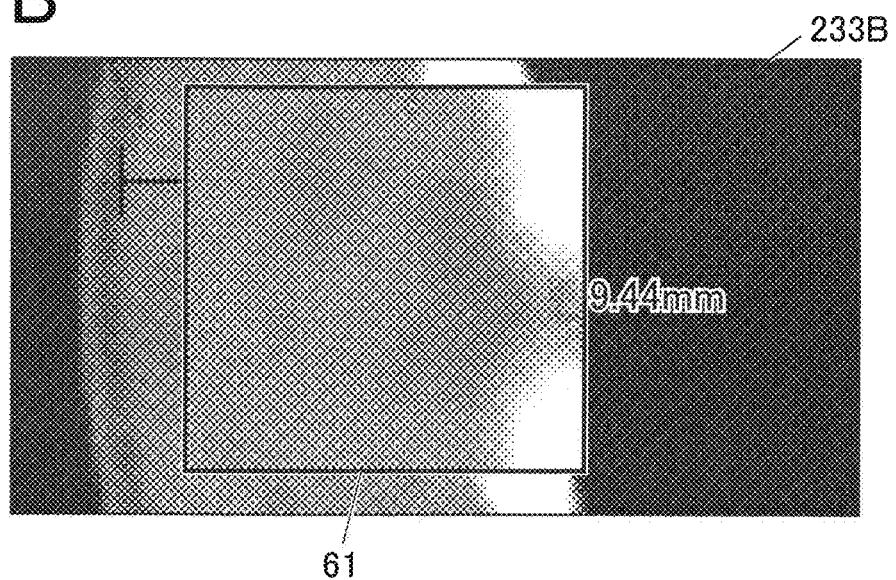
FIG. 7B is another example of a viewer screen in which the magnifying glass function is being executed.

On a viewer screen 233B illustrated in FIG. 7B, a prescribed region of the medical image centered on the touch position is enlarged by a predetermined enlargement ratio, so that an enlarged image 61 is displayed in the medical image in a superimposed manner. When the user moves the touch position with his/her finger kept on the touch panel 22B while the magnifying glass function is being executed, the center position of the region being displayed in enlargement moves.

After the process at step S17, step S22, or step S27 is performed, the first object selecting process ends.

As explained above, according to the first embodiment, as being triggered by the long touch operation, such selectable objects that are included in the prescribed range from the position in the medical image corresponding to the position of the long touch operation are extracted as the selected candidates. The extracted selected candidates are sequentially arranged to be in the selected state in accordance with the touch time periods on the touch panel 22B, so as to confirm the selection of each of the selected candidates that was in the selected state at the time of the finger-off operation. It is therefore possible to improve operability in the process of selecting the selectable objects from the medical image. Although it is difficult to designate a position in a fine-tuned manner on the touch panel 22B, it is possible to clearly indicate which one of the selected candidates is in the selected state, by sequentially changing the display modes of the selected candidates in accordance with the touch time periods.

Further, when the selection of the annotation or the measurement line has been confirmed, it is possible to correct the position or the size of the annotation or the measurement line.

Further, when the selection of any of the processing functions has been confirmed, it is possible to execute the prescribed processing function by performing the prescribed operation on the touch panel 22B.

Second Embodiment

A medical image display system according to a second embodiment has a configuration similar to that of the medical image display system 100 described in the first embodiment. Thus, FIG. 1 will be referenced, and the explanations of some of the constituent elements that are the same as those in the first embodiment will be omitted. In the following sections, constituent elements and processes that are characteristic to the second embodiment will be explained.

When a long touch operation is performed on the touch panel 22B while a medical image is being displayed on the display unit 23, the controller 21 included in the medical image display apparatus 20 refers to the object position information (the annotation data, the measurement line data, and the processing function data) and extracts, from among the plurality of selectable objects, such selectable objects that are included in a prescribed range from the position in the medical image corresponding to the position of the long touch operation, as selected candidates.

In accordance with the touch position of the long touch operation performed on the touch panel 22B, the controller 21 sequentially arranges the extracted selected candidates to be in a selected state. More specifically, in accordance with the distance of a move from the position where the long touch operation was started, the controller 21 switches the selected candidate being in the selected state from one selected candidate to another. The moving direction may be an up-and-down direction, a left-and-right direction, or the like and is not particularly limited.

When a finger-off operation is performed on the touch panel 22B, the controller 21 confirms the selection of the selected candidate that is in the selected state at the time of the finger-off operation.

With reference to FIGS. 8A to 8E, a method for moving a touch position on the touch panel 22B will be explained. In the present example, it is assumed that a user moves his/her finger in an up-and-down direction on the touch panel 22B.

FIG. 8A illustrates a position P1 in which the user started a long touch operation.

FIG. 8B illustrates a position P2 reached by moving upward from the position P1 illustrated in FIG. 8A by a predetermined amount. It is possible to arbitrarily set the predetermined amount (the moving distance) used as a threshold value for recognizing the move of the finger.

FIG. 8C illustrates a position P3 reached by moving further upward from the position P2 illustrated in FIG. 8B by a predetermined amount.

FIG. 8D illustrates a position P4 (the same position as the position P2 illustrated in FIG. 8B) reached by moving downward from the position P3 illustrated in FIG. 8C by the predetermined amount.

FIG. 8E illustrates a position P5 (the same position as the position P1 illustrated in FIG. 8A) reached by moving further downward from the position P4 illustrated in FIG. 8D by the predetermined amount.

In the second embodiment, the position P1 (P5) is kept in correspondence with the first selected candidate, whereas the position P2 (P4) is kept in correspondence with the second selected candidate, and the position P3 is kept in correspondence with the third selected candidate, so that the selected candidate being in the selected state is switched from one to another, as a result of moving the finger positioned on the touch panel 22B without taking the finger off the touch panel 22B.

Next, operations in the second embodiment will be explained.

In the second embodiment also, the preliminary preparing process (see FIG. 3) is the same as that in the first embodiment.

Figure 9:
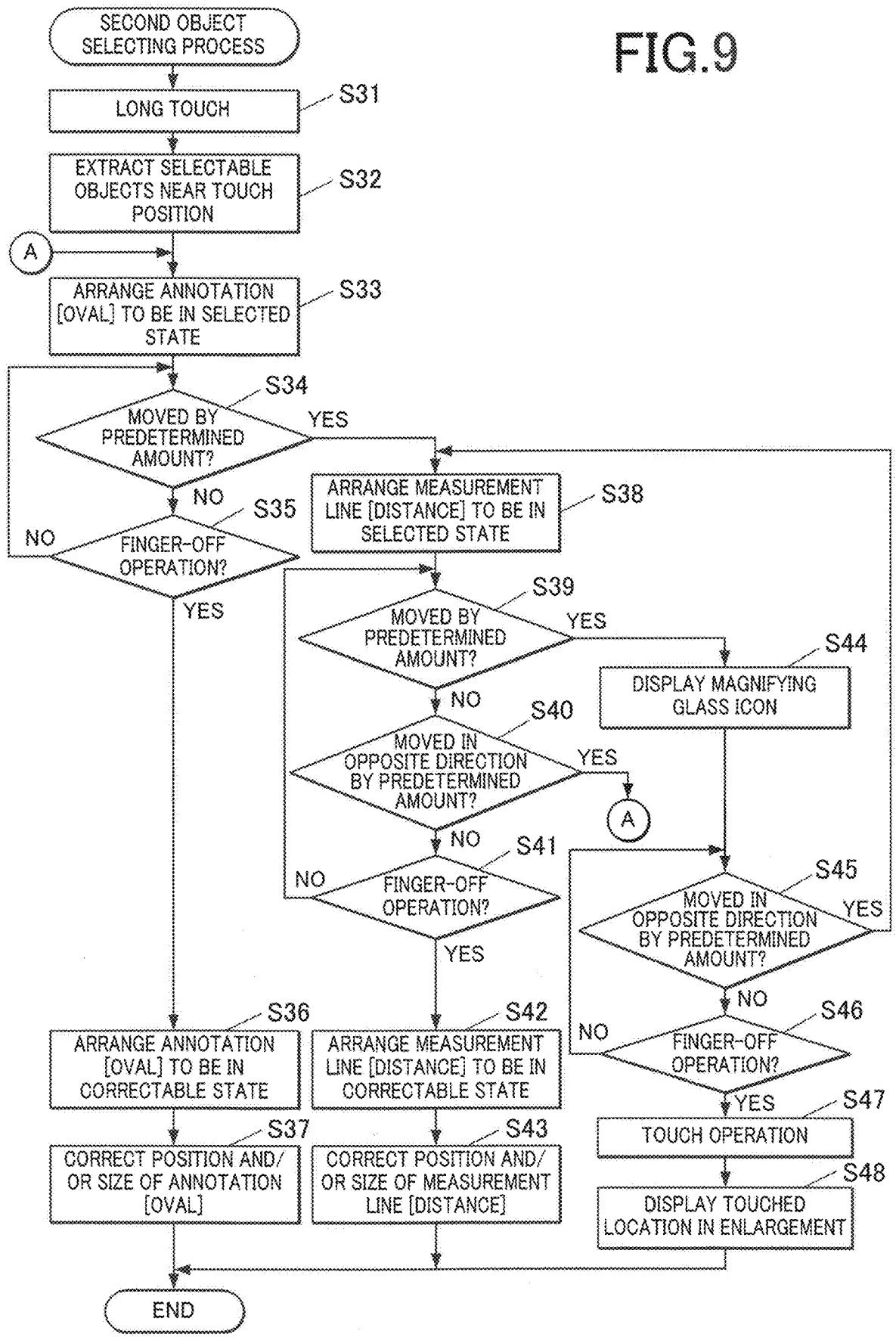
FIG. 9 is a flowchart illustrating a second object selecting process.

FIG. 9 is a flowchart illustrating a second object selecting process performed by the medical image display apparatus 20. This process is performed subsequent to the preliminary preparing process and is realized by a software process implemented by collaboration between the controller 21 and a program stored in the storage unit 26.

The processes performed at steps S31 through S33 are the same as the processes performed at steps S11 through S13 illustrated in FIG. 4.

For an example of a viewer screen in which the oval annotation is in the selected state, see FIG. 5A.

Subsequently, the controller 21 judges whether or not the touch position has moved by the predetermined amount since the oval annotation was brought into the selected state, on the basis of the touch position on the touch panel 22B (step S34). For example, the controller 21 judges whether or not the touch position has moved from the position P1 illustrated in FIG. 8A to the position P2 illustrated in FIG. 8B.

When it is determined that the touch position has not moved by the predetermined amount since the oval annotation was brought into the selected state (step S34: No), the controller 21 judges whether or not a finger-off operation has been performed on the touch panel 22B by the user (step S35).

When the finger-off operation has not been performed (step S35: No), the process returns to step S34, so that the processing is repeatedly performed.

On the contrary, when it is determined at step S35 that the finger-off operation has been performed (step S35: Yes), the controller 21 confirms the selection of the oval annotation that was in the selected state at the time of the finger-off operation and further arranges the oval annotation to be in a correctable state (step S36) (see FIG. 5B).

Subsequently, according to an operation performed on the touch panel 22B by the user, the controller 21 corrects the position and/or the size of the oval annotation (step S37) (see FIG. 5C).

When it is determined at step S34 that the touch position has moved by the predetermined amount since the oval annotation was brought into the selected state (step S34: Yes), the controller 21 arranges the distance measurement line displayed on the display unit 23 to be in a selected state (step S38) (see FIG. 6A).

Subsequently, on the basis of the touch position on the touch panel 22B, the controller 21 judges whether or not the touch position has moved by the predetermined amount (in the same direction as in the situation where step S34: Yes) since the distance measurement line was brought into the selected state (step S39). For example, the controller 21 judges whether or not the touch position has moved from the position P2 illustrated in FIG. 8B to the position P3 illustrated in FIG. 8C.

When the touch position has not moved by the predetermined amount since the distance measurement line was brought into the selected state (step S39: No), the controller 21 judges, on the basis of the touch position on the touch panel 22B, whether or not the touch position has moved by the predetermined amount in the opposite direction (to the direction in the situation where step S34: Yes) since the distance measurement line was brought into the selected state (step S40). For example, the controller 21 judges whether or not the touch position has moved from the position P2 illustrated in FIG. 8B to the position P1 illustrated in FIG. 8A.

When it is determined that the touch position has moved by the predetermined amount in the opposite direction since the distance measurement line was brought into the selected state (step S40: Yes), the process returns to step S33 (see FIG. 5A).

When it is determined at step S40 that the touch position has not moved by the predetermined amount in the opposite direction since the distance measurement line was brought into the selected state (step S40: No), the controller 21 judges whether or not a finger-off operation has been performed on the touch panel 22B by the user (step S41).

When the finger-off operation has not been performed (step S41: No), the process returns to step S39, so that the processing is repeatedly performed.

When it is determined at step S41 that the finger-off operation has been performed (step S41: Yes), the controller 21 confirms the selection of the distance measurement line that was in the selected state at the time of the finger-off operation and further arranges the distance measurement line to be in a correctable state (step S42) (see FIG. 6B).

Subsequently, the controller 21 corrects the position and/or the size of the distance measurement line according to an operation performed on the touch panel 22B by the user (step S43) (see FIG. 6C).

When it is determined at step S39 that the touch position has moved by the predetermined amount since the distance measurement line was brought into the selected state (step S39: Yes), the controller 21 arranges the magnifying glass function to be in a selected state and causes the display unit 23 to display a magnifying glass icon (step S44) (see FIG. 7A).

After that, on the basis of the touch position on the touch panel 22B, the controller 21 judges whether or not the touch position has moved by the predetermined amount in the opposite direction (to the direction in the situation where step S34: Yes) since the magnifying glass icon was displayed (step S45). For example, the controller 21 judges whether or not the touch position has moved from the position P3 illustrated in FIG. 8C to the position P4 illustrated in FIG. 8D. In this situation, when the selected candidates have each been brought into the selected state up to the maximum number of selected candidates (three in the present example), the selected candidate will not be changed thereafter even if the distance from the start position of the long touch operation is further increased.

On the contrary, when the touch position has moved by the predetermined amount in the opposite direction since the magnifying glass icon was displayed (step S45: Yes), the process returns to step S38 (see FIG. 6A).

When it is determined at step S45 that the touch position has not moved by the predetermined amount in the opposite direction since the magnifying glass icon was displayed (step S45: No), the controller 21 judges whether or not a finger-off operation has been performed on the touch panel 22B by the user (step S46).

When the finger-off operation has not been performed (step S46: No), the process returns to step S45, so that the processing is repeatedly performed.

When it is determined at step S46 that the finger-off operation has been performed (step S46: Yes), the controller 21 confirms the selection of the magnifying glass function that was in the selected state at the time of the finger-off operation and arranges the magnifying glass function to be in an executable state.

When a touch operation is performed on the touch panel 22B by the user (step S47), the controller 21 displays, in enlargement, the touched location of the medical image (step S48) (see FIG. 7B).

After the process at step S37, step S43, or step S48 is performed, the second object selecting process ends.

As explained above, according to the second embodiment, as being triggered by the long touch operation, such selectable objects that are included in the prescribed range from the position in the medical image corresponding to the position of the long touch operation are extracted as the selected candidates. The extracted selected candidates are sequentially arranged to be in the selected state in accordance with the touch positions on the touch panel 22B, so as to confirm the selection of each of the selected candidates that was in the selected state at the time of the finger-off operation. It is therefore possible to improve operability in the process of selecting the selectable objects from the medical image. Although it is difficult to designate a position in a fine-tuned manner on the touch panel 22B, it is possible to clearly indicate which one of the selected candidates is in the selected state, by sequentially changing the display modes of the selected candidates in accordance with the touch positions.

Third Embodiment

A medical image display system according to a third embodiment has a configuration similar to that of the medical image display system 100 described in the first embodiment. Thus, FIG. 1 will be referenced, and the explanations of some of the constituent elements that are the same as those in the first embodiment will be omitted. In the following sections, constituent elements and processes that are characteristic to the third embodiment will be explained.

The touch panel 22B included in the medical image display apparatus 20 is capable of detecting, not only the touch position on the plane, but also differences in touch depths exhibited by pressing of a finger of the user, or the like. The touch panel 22B detects the touch depths on three levels (small, medium, and large) and outputs a detection result to the controller 21.

When a long touch operation is performed on the touch panel 22B while a medical image is being displayed on the display unit 23, the controller 21 refers to the object position information (the annotation data, the measurement line data, and the processing function data) and extracts, from among the plurality of selectable objects, such selectable objects that are included in a prescribed range from the position in the medical image corresponding to the position of the long touch operation, as selected candidates.

In accordance with the touch depth of the long touch operation performed on the touch panel 22B, the controller 21 sequentially arranges the extracted selected candidates to be in a selected state.

When a finger-off operation is performed on the touch panel 22B, the controller 21 confirms the selection of the selected candidate that is in the selected state at the time of the finger-off operation.

In the third embodiment, the touch depth "small" is kept in correspondence with the first selected candidate, whereas the touch depth "medium" is kept in correspondence with the second selected candidate, and the touch depth "large" is kept in correspondence with the third selected candidate, so that the selected candidate being in the selected state is switched from one to another, as a result of changing the touch depth on the touch panel 22B.

Next, operations in the third embodiment will be explained.

In the third embodiment also, the preliminary preparing process (see FIG. 3) is the same as that in the first embodiment.

Figure 10:
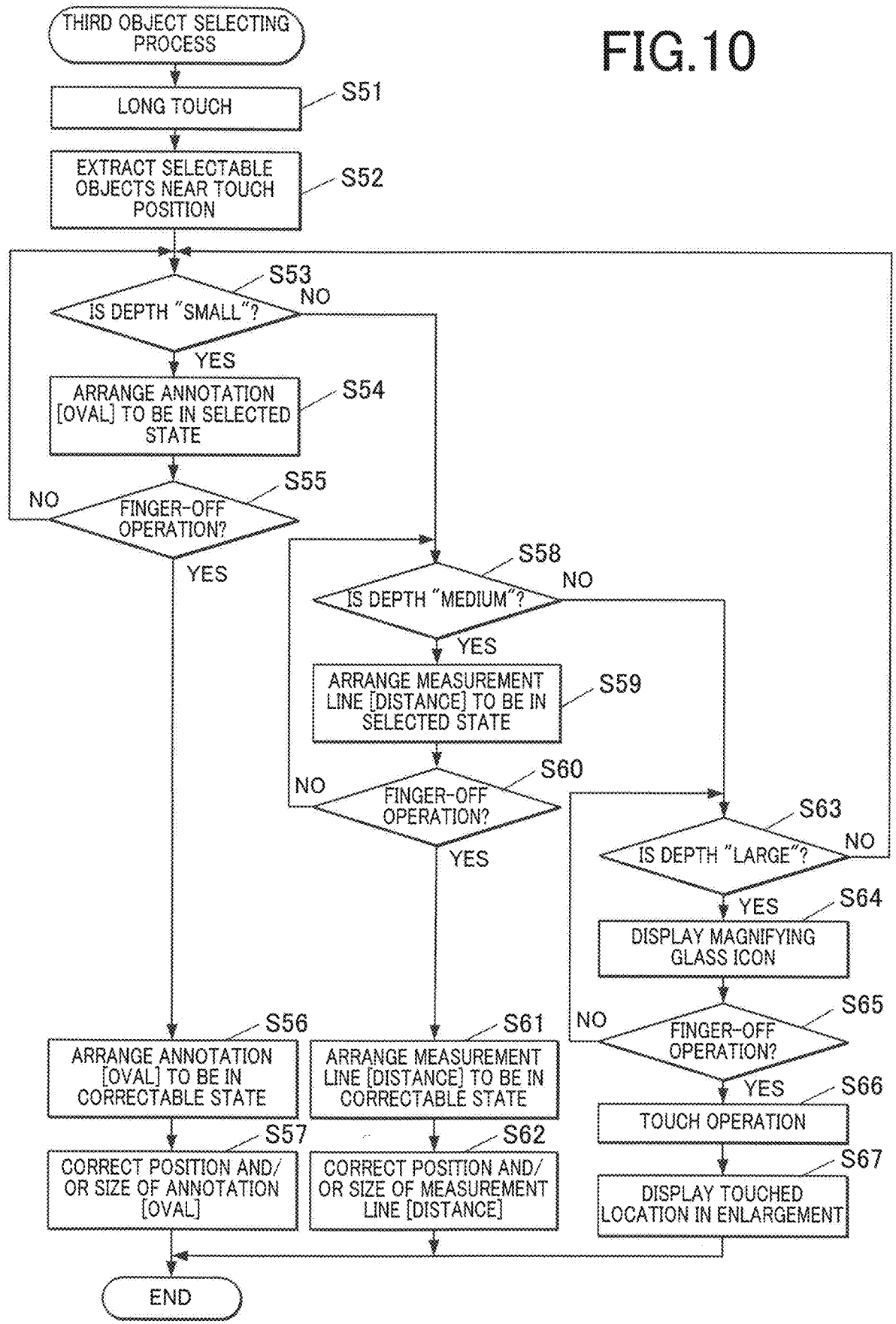
FIG. 10 is a flowchart illustrating a third object selecting process according to a third embodiment.

FIG. 10 is a flowchart illustrating a third object selecting process performed by the medical image display apparatus 20. This process is performed subsequent to the preliminary preparing process and is realized by a software process implemented by collaboration between the controller 21 and a program stored in the storage unit 26.

The processes performed at steps S51 through S52 are the same as the processes performed at steps S11 through S12 illustrated in FIG. 4.

Subsequently, the controller 21 judges whether or not the touch depth on the touch panel 22B is "small" (step S53).

When the touch depth is "small" (step S53: Yes), the controller 21 arranges the oval annotation displayed on the display unit 23 to be in a selected state (step S54) (see FIG. 5A).

After that, the controller 21 judges whether or not a finger-off operation has been performed on the touch panel 22B by the user (step S55).

When the finger-off operation has not been performed (step S55: No), the process returns to step S53, so that the processing is repeatedly performed.

When it is determined at step S55 that the finger-off operation has been performed (step S55: Yes), the controller 21 confirms the selection of the oval annotation that was in the selected state at the time of the finger-off operation and further arranges the oval annotation to be in a correctable state (step S56) (see FIG. 5B).

Subsequently, the controller 21 corrects the position and/or the size of the oval annotation according to an operation performed on the touch panel 22B by the user (step S57) (see FIG. 5C).

When it is determined at step S53 that the touch depth is not "small" (step S53: No), the controller 21 judges whether or not the touch depth on the touch panel 22B is "medium" (step S58).

When the touch depth is "medium" (step S58: Yes), the controller 21 arranges the distance measurement line displayed on the display unit 23 to be in a selected state (step S59) (see FIG. 6A).

After that, the controller 21 judges whether or not a finger-off operation has been performed on the touch panel 22B by the user (step S60).

When the finger-off operation has not been performed (step S60: No), the process returns to step S58, so that the processing is repeatedly performed.

When it is determined at step S60 that the finger-off operation has been performed (step S60: Yes), the controller 21 confirms the selection of the distance measurement line that was in the selected state at the time of the finger-off operation and further arranges the distance measurement line to be in a correctable state (step S61) (see FIG. 6B).

Subsequently, the controller 21 corrects the position and/or the size of the distance measurement line according to an operation performed on the touch panel 22B by the user (step S62) (see FIG. 6C).

When it is determined at step S58 that the touch depth is not "medium" (step S58: No), the controller 21 judges whether or not the touch depth on the touch panel 22B is "large" (step S63).

When the touch depth is not "large" (step S63: No), the process returns to step S53.

When it is determined at step S63 that the touch depth is "large" (step S63: Yes), the controller 21 arranges the magnifying glass function to be in a selected state and causes the display unit 23 to display a magnifying glass icon (step S64) (see FIG. 7A).

After that, the controller 21 judges whether or not a finger-off operation has been performed on the touch panel 22B by the user (step S65).

When the finger-off operation has not been performed (step S65: No), the process returns to step S63, so that the processing is repeatedly performed.

When it is determined at step S65 that the finger-off operation has been performed (step S65: Yes), the controller 21 confirms the selection of the magnifying glass function that was in the selected state at the time of the finger-off operation and further arranges the magnifying glass function to be in an executable state.

When a touch operation is performed on the touch panel 22B by the user (step S66), the controller 21 displays, in enlargement, the touched location of the medical image (step S67) (see FIG. 7B).

After the process at step S57, step S62, or step S67 is performed, the third object selecting process ends.

As explained above, according to the third embodiment, as being triggered by the long touch operation, such selectable objects that are included in the prescribed range from the position in the medical image corresponding to the position of the long touch operation are extracted as the selected candidates. The extracted selected candidates are sequentially arranged to be in the selected state in accordance with the touch depths on the touch panel 22B, so as to confirm the selection of each of the selected candidates that was in the selected state at the time of the finger-off operation. It is therefore possible to improve operability in the process of selecting the selectable objects from the medical image. Although it is difficult to designate a position in a fine-tuned manner on the touch panel 22B, it is possible to clearly indicate which one of the selected candidates is in the selected state, by sequentially changing the display modes of the selected candidates in accordance with the touch depths.

The description of the embodiments above pertains to examples of a medical image display apparatus according to the present invention; however, the present disclosure is not limited to these examples. It is also possible to modify, as appropriate, any of the detailed configurations and the detailed operations of the constituent elements of the apparatus, as long as the modification does not depart from the scope of the present invention.

For example, the annotation, the measurement line, and the selectable processing function drawn in a medical image are not limited to the examples described above. Further, there is no particular limitation to the quantity of the selectable objects that are kept in correspondence with each medical image and to the quantity of the selected candidates extracted therefrom.

Further, the embodiments above are explained while a focus is placed on the image processing function used as the prescribed processing function serving as a selectable object. However, the present disclosure is similarly applicable to the annotation drawing function and the measuring function. More specifically, when another annotation is to be further drawn while an annotation or a measurement line has already been drawn, the user is to select an icon corresponding to the annotation drawing function. In that situation, it is possible to extract an annotation, a measurement line, and the annotation drawing function that are present in a prescribed range from the position in the medical image corresponding to the position of a long touch operation, as selected candidates. When the selection of the annotation drawing function (a line, an arrow, a rectangle, a polygon, an oval, or the like) has been confirmed, a prescribed operation (e.g., designation of a position) performed on the touch panel 22B is allocated to an event that executes the annotation drawing function. Further, when the selection of the measuring function has been confirmed, a prescribed operation (e.g., designation of a position in which a measurement line is to be drawn) performed on the touch panel 22B is allocated to an event that executes the measuring function (e.g., to draw the measurement line, to calculate a measured value, and to draw the measured value).

In the description above, the example is disclosed in which a hard disk or a nonvolatile semiconductor memory is used as a computer-readable medium storing therein the program used for executing the processes. However, possible embodiments are not limited to this example. It is also possible to use a portable recording medium such as a CD-ROM as another type of computer-readable medium. Further, it is also acceptable to use a carrier wave as a medium used for providing data of the program via a communication line.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-059119, filed on Mar. 27, 2018, is incorporated herein by reference in its entirety.

What is claimed is:

1. A medical image display apparatus comprising:
    a displayer which comprises a display screen displaying a medical image;
    a touch panel provided on the display screen of the displayer;
    a storage which, with respect to the medical image, stores therein object position information which keeps a plurality of selectable objects in correspondence with positions thereof; and
    a hardware processor which, when a long touch operation is performed on the touch panel while the medical image is being displayed on the displayer, refers to the object position information and extracts, from among the plurality of selectable objects, such selectable objects that are included in a prescribed range from a position in the medical image corresponding to a position of the long touch operation, as selected candidates, further arranges the extracted selected candidates sequentially to be in a selected state in accordance with a touch time period, a touch position, or a touch depth on the touch panel, and when a finger-off operation is performed on the touch panel, confirms selection of any of the selected candidates which is in the selected state at a time of the finger-off operation.

2. The medical image display apparatus according to claim 1, wherein
    the selectable objects are each either an annotation or a measurement line drawn in the medical image.

3. The medical image display apparatus according to claim 2, wherein
    the hardware processor corrects either a position or a size of any of the selected candidates of which the selection is confirmed, on a basis of an operation performed on the touch panel.

4. The medical image display apparatus according to claim 1, wherein
    the selectable objects are each a processing function to perform a prescribed process on the medical image.

5. The medical image display apparatus according to claim 4, wherein
    the confirmation of the selection of the processing function is to allocate a prescribed operation performed on the touch panel to an event which executes the processing function.

6. A non-transitory computer-readable recording medium storing a program causing a computer of a medical image display apparatus to perform processes, wherein the medical image display apparatus includes a displayer which comprises a display screen displaying a medical image, a touch panel provided on the display screen of the displayer, a storage which, with respect to the medical image, stores therein object position information which keeps a plurality of selectable objects in correspondence with positions thereof, the processes comprising:
    referring to the object position information, when a long touch operation is performed on the touch panel while the medical image is being displayed on the displayer;
    extracting, from among the plurality of selectable objects, such selectable objects that are included in a prescribed range from a position in the medical image corresponding to a position of the long touch operation, as selected candidates;
    arranging the extracted selected candidates sequentially to be in a selected state in accordance with a touch time period, a touch position, or a touch depth on the touch panel; and
    confirming, when a finger-off operation is performed on the touch panel, selection of any of the selected candidates which is in the selected state at a time of the finger-off operation.

* * * * *